US008187884B2

(12) United States Patent
Ohta et al.

(10) Patent No.: US 8,187,884 B2
(45) Date of Patent: *May 29, 2012

(54) METHOD OF ENHANCING HOMOLOGOUS RECOMBINATION OF SOMATIC CELLS AND METHOD OF CONSTRUCTING SPECIFIC ANTIBODY

(75) Inventors: Kunihiro Ohta, Saitama (JP); Hidetaka Seo, Saitama (JP); Takehiko Shibata, Saitama (JP)

(73) Assignees: Riken, Saitama (JP); Chiome Bioscience, Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/813,454

(22) Filed: Jun. 10, 2010

(65) Prior Publication Data

US 2011/0070650 A1 Mar. 24, 2011

Related U.S. Application Data

(63) Continuation of application No. 10/522,644, filed as application No. PCT/JP03/09563 on Jul. 28, 2003, now Pat. No. 7,776,599.

(30) Foreign Application Priority Data

Jul. 30, 2002 (JP) ................................. 2002-221232

(51) Int. Cl.
 *C12N 15/09* (2006.01)
 *C12N 15/85* (2006.01)
 *C12N 5/0781* (2010.01)
(52) U.S. Cl. ...................... 435/455; 435/70.21; 435/326; 435/349
(58) Field of Classification Search .................. 435/455, 435/70.21, 326, 349
See application file for complete search history.

(56) References Cited

FOREIGN PATENT DOCUMENTS

| WO | WO 00/22111 | 4/2000 |
| WO | WO 02/100998 | 12/2002 |
| WO | WO 03/095636 | 11/2003 |

OTHER PUBLICATIONS

Agata, Y. et al., "Histone Acetylation Determines the Developmentally Regulated Accessibility for T Cell Receptor Gamma Gene Recombination", *J. Exp. Med.*, 2001, pp. 873-880, vol. 193, No. 7.
Arakawa and Buerstedde, "Immunoglobulin Gene Conversion: Insights From Bursal B Cells and the DT40 Cell Line", *Developmental Dynamics*, 2004, pp. 458-464, vol. 229.
Bai et al., "Free Radical Mechanism of Proliferation of Peripheral Blood Lymphocytes Cultured with Monocytes", *Journal of Cell Biology*, 2002, pp. 187-188, vol. 24, No. 3.
Bassing et al., "The mechanism and regulation of chromosomal V(D)J recombination", *Cell*, Apr. 2002, pp. S45-S55, vol. 109.
Buerstedde, JM. et al., "Light chain gene conversion continues at high rate in an ALV-induced cell line", *The EMBO Journal*, 1990, pp. 921-927, vol. 9, No. 3.
Chauhan et al., "Construction of a new universal vector for insertional mutagenesis by homologous recombination", *Gene*, 1992, pp. 281-286, vol. 120.
Chinese Office Action, issued Jul. 21, 2006 in connection with Patent Application No. 03818205.X (refers to *Chinese Journal of Hematology*, Jun. 2002, vol. 23, No. 6).
*Chinese Journal of Hematology*, Jun. 2002, vol. 23, No. 6.
Cumbes, S.J. et al., "Generation and interactive affinity maturation of antibodies in vitro using hypermutating B-cell lines", *Nat. Biotechnol.*, Nov. 2002, pp. 1129-1134, vol. 20, No. 11.
Grawunder et al., "DNA Ligase IV is Essential for V(D)J Recombination and DNA Double-Strand Break Repair in Human Precursor Lymphocytes", *Molecular Cell*, Oct. 1998, pp. 477-484, vol. 2.
Jones et al., "The taming of a transposon: V(D)J recombination and the immune system", *Immunological Reviews*, 2004, pp. 233-248, vol. 200.
Kelly, William K. et al., "Histone deacetylase inhibitors: from target to clinical trials", *Expert Opinion on Investigational Drugs*, Dec. 1, 2002, pp. 1695-1713, vol. 11, No. 12, Ashley Publications Ltd., London, GB, XP001202636, ISSN: 1354-3784.
Kramer, Oliver H. et al., "Histone deacetylase as a therapeutic target", *Trends in Endocrinology and Metabolism*, Elsevier Science Publishing, New York, NY, US, Sep. 2001, pp. 294-300, vol. 12, No. 7, XP002329890, ISSN: 1043-2760.
Marks, Paul A. et al., "Histone deacetylase inhibitors as new cancer drugs", *Current Opinion in Oncology*, Current Science Ltd., US, 2001, pp. 477-483, vol. 13, No. 6, XP009010050, ISSN: 1040-8746.
Mathieu, et al., "Chromatin remodeling by the T-cell receptor (TCR)-β gene enchancer during early T cell development: implications for the control of TCR-β locus recombination", *J. Exp. Med.*, Sep. 4, 2000, pp. 625-636, vol. 192, No. 5.
Sale, J.E. et al., "Ablation of XRCC2/3 transforms immunoglobulin V gene conversion into somatic hypermutation", *Nature*, 2001, pp. 921-926, vol. 412, No. 6850.
Sale, Julian E et al., "TdT-Accessible Breaks are Scattered over the Immunoglobulin V Domain in a Constitutively Hypermutating B Cell Line", *Immunity*, Cell Press, US, 1998, pp. 859-869, vol. 9, No. 6, XP000876807, ISSN: 1074-7613.

(Continued)

*Primary Examiner* — Maria Leavitt
(74) *Attorney, Agent, or Firm* — Finnegan, Henderson, Farabow, Garrett & Dunner, LLP (57) ABSTRACT

The present invention provides a novel method for obtaining diverse antibodies as a result of markedly enhancing the somatic homologous recombination at an antibody locus in immunocytes.
By putting immunocytes in which DNA homologous recombination is occurring at an antibody locus (for example, DT40 cells and the like) into contact and the like with histone acetylase inhibitor and the like (for example, trichostatin A and the like), thereby relaxing the chromatin structure at said antibody locus, somatic homologous recombination at an antibody locus is enhanced, and the production of diverse antibody molecules is made possible.
The production of antibodies that bind specifically to antigens from cell populations in which the antibody molecules have been diversified by the enhancement of somatic homologous recombination is made possible by using an appropriate selection method (for example, beads coated with antigen and the like).

8 Claims, 10 Drawing Sheets

OTHER PUBLICATIONS

Seo et al, "Rapid generation of specific antibodies by enhanced homologous recombination", *Nature Biotechnology*, Jun. 2005, pp. 731-735, vol. 23, No. 6.

Senoo et al., "Limited effect of chromatin remodeling on D$\beta$-to-J$\beta$ recombination in CD4+ CD8+ thymocyte: implications for a new aspect in the regulation of TCR $\beta$ gene recombination", *International Immunology*, Aug. 3, 2001, pp. 1405-1414, vol. 12, No. 11.

Shibata, "Functions of homologous DNA recombination" *RIKEN Review No. 41: Focused on Bioarchitect Research*, Nov. 2001, pp. 21-23.

Yasunari, Takami et al., "Chicken Histone Deacetylase-2 Controls the Amount of the IgM H-chain at the Steps of Both Transcription of Its Gene and Alternative Processing of Its Pre-mRNA in the DT40 Cell Line", *The Journal of Biological Chemistry*, Aug. 20, 1999, pp. 23977-23990, vol. 274, No. 34.

Chinese Office Action, dated Feb. 22, 2008 in connection with Patent Application No. 200380110005.X; concise English-language explanation attached.

European Office Action issued Mar. 26, 2009 in connection with counterpart EP Application No. 03771393.0.

English Translation of International Preliminary Examination Report for PCT/JP03/09563, dated Apr. 28, 2005.

International Preliminary Examination Report (PCT/IPEA/409) of PCT/JP03/09563.

Figure 1

V: Variable Region
J: Junction Region
C: Constant Region
E: EcoRI Site
bsr: blasticidin resistance gene

CDR: Complementary Determining Region
Inside () are number of clones

▬ : gene conversion, numeral is number of false gene
● : point mutation
○ : single base deletion
▭ : oligonucleotide deletion
▽ : base insertion

Vertical Axis: Number of Cells
Horizontal Axis: Fluorescence Intensity

Figure 5

Vertical Axis: Number of Cells
Horizontal Axis: Fluorescence Intensity

Figure 6(a)

Vertical Axis: Number of Cells
Horizontal Axis: Fluorescence Intensity

Figure 6(c)

SEQUENCE LISTING

<160> NUMBER OF SEQ ID NOS: 4

<210> SEQ ID NO 1
<211> LENGTH: 19
<212> TYPE: DNA
<213> ORGANISM: artificial
<220> FEATURE:
<223> OTHER INFORMATION: Designed nucleotide for PCR amplification

<400> SEQUENCE: 1
atcttgcctt cctcatggc                                          19

<210> SEQ ID NO 2
<211> LENGTH: 19
<212> TYPE: DNA
<213> ORGANISM: artificial

-continued

```
<220> FEATURE:
<223> OTHER INFORMATION: Designed nucleotide for PCR amplification

<400> SEQUENCE: 2
gtttgggtga acgtggttc                                                 19

<210> SEQ ID NO 3
<211> LENGTH: 22
<212> TYPE: DNA
<213> ORGANISM: Gallus gallus
<220> FEATURE:
<221> NAME/KEY: primer_bind
<222> LOCATION: (1)..(22)

<400> SEQUENCE: 3
cacacctcag gtactcgttg cg                                             22

<210> SEQ ID NO 4
<211> LENGTH: 21
<212> TYPE: DNA
<213> ORGANISM: Gallus gallus
<220> FEATURE:
<221> NAME/KEY: primer_bind
<222> LOCATION: (1)..(21)

<400> SEQUENCE: 4
tcagcgactc acctaggacg g                                              21
```

METHOD OF ENHANCING HOMOLOGOUS RECOMBINATION OF SOMATIC CELLS AND METHOD OF CONSTRUCTING SPECIFIC ANTIBODY

RELATED APPLICATIONS

This application is a continuation of U.S. application Ser. No. 10/522,644, now U.S. Pat. No. 7,776,599, filed Feb. 28, 2005, issue date Aug. 17, 2010, entitled METHOD OF ENHANCING HOMOLOGOUS RECOMBINATION OF SOMATIC CELLS AND METHOD OF CONSTRUCTING SPECIFIC ANTIBODY, which is a U.S. national stage application under 35 U.S.C. §371 of International Application No. PCT/JP2003/09563, filed Jul. 28, 2003, and claims the benefit of Japanese Patent Application No. 2002-221232, filed Jul. 30, 2002, all of which are incorporated herein by reference in their entirety.

TECHNICAL FIELD

The present invention concerns generally a technology that enhances the homologous recombination of somatic cells and relates in more detail to a method that enhances the homologous recombination of somatic cells at a genetic locus in a somatic cell, and immunocytes wherein somatic homologous recombination has been enhanced by said method.

Additionally, the present invention relates to a method of acquiring diverse antibody molecules by using the aforementioned enhancing method for somatic homologous recombination, and diverse antibodies constructed by said method.

Further, the present invention relates to a medicinal agent suitable for using to promote somatic homologous recombination.

BACKGROUND TECHNOLOGY

Conventionally, somatic homologous recombination is thought of as one factor that produces genetic diversity. For example, in a chicken-derived B cell lines, it is known that DNA recombination occurs at immunoglobulin locus for antibodies (Buerstedde et al., EMBO J. (1990) 9:921-927). Creating various protein factors using such DNA recombination is thinkable, but in actuality, the recombination frequency is extremely low, so it was difficult to use by itself for the creation of protein factors.

Additionally, when producing antibodies, animals such as rabbits and mice are normally used, but in cases where it is desired for even more diverse antibodies to be obtained, it was necessary to immunize a large number of individual animals with the antigens. Additionally, the titers of antibodies obtained depended on differences between individual animals, and the properties of the antigens, so that it was difficult to stably obtain diverse antibodies at high titers.

Consequently, obtaining antibodies by using DNA homologous recombination that occurs in the aforementioned chicken-derived B cell lines and the like was conceived of, and it is thought that in principle, it would become possible to synthesize diverse antibodies with this method. However, as described above, since the DNA homologous recombination frequency is extremely low, it was thought that it was extremely difficult in reality to artificially create antibodies for specific antigens with cultured cells.

On the other hand, in recent years, in XRCC2 and XRCC3 knockout DT40 cell lines (chicken-derived B cell lines), it has been reported that the frequency of somatic cell mutation increases (Sale et al., Nature (2001) 412:921:926). The use of such somatic cell mutations has been considered, and in actuality, attempts have been made to increase antibody affinity to antigens by using Ramos cells and XRCC2 and XRCC3 knockout DT40 cells. However, antibodies obtained using such methods show no specificity, and bind to various proteins (Cumbers et al., Nat. Biotechnol. (2002) 20 (11):1129-1134). Since somatic cell mutations have a secondary use in vivo for affinity maturation, it is thought that making large-scale changes in antibody specificity would be difficult.

DISCLOSURE OF THE INVENTION

The inventors of the present invention, in view of the abovementioned state of affairs, as a result of dedicated research into whether there is a method of inducing or enhancing the desired somatic homologous recombination under controlled conditions, found, contrary to expectations, that it is possible to raise the frequency of somatic homologous recombination greatly by relaxing the chromatin structure of immunocyte chromosomes.

In this way, the present invention has, in general, the purpose of providing a method to enhance somatic homologous recombination at a genetic locus in somatic cells.

Additionally, the present invention has the purpose of providing an immunocyte wherein somatic homologous recombination has been promoted in the abovementioned method.

Further, the present invention has the purpose of providing an antibody production method that makes it possible to obtain diverse antibodies by using somatic homologous recombination that occurs in immunocytes.

Still further, the present invention has the purpose of providing a diverse antibodies produced by the abovementioned antibody production method.

Therefore, in the present invention, a method is provided for promoting somatic homologous recombination, characterized by the promotion of homologous recombination in somatic cells in which DNA homologous recombination is occurring at a genetic locus, by relaxing the chromatin structure of chromosomes in said somatic cells.

Additionally, in the present invention, an antibody production method characterized in that in producing antibodies from immunocytes wherein DNA homologous recombination is occurring at a genetic locus, by relaxing the chromatin structure of chromosomes in said immunocytes, DNA homologous recombination at antibody locus is enhanced, whereby a diverse antibodies are obtained. Additionally, diverse antibodies produced in this method are provided.

From the standpoint of obtaining a diversity of antibody genes, it is known that homologous recombination has a higher efficiency than mutation, and in comparison with XRCC2/XRCC3 variant strains (Sale et al., Nature (2001) 412:921-926), it is thought that antibodies with a high diversity are more easily obtainable. If a cell is obtained wherein somatic homologous recombination at an antibody locus is enhanced, and which produces the desired antibody, by culturing and maintaining said cells, it will become possible to prepare the desired antibody easily at any time. Therefore, in the future, the establishment of technology for producing antibodies at high titers against all antigens without the use of animal experiments may be expected, and it will become possible to provide antibodies and the like that are useful for the treatment of diseases and the like at high titers and continuously. Additionally, it is thought that this has utility from the standpoint of humanity towards animals.

The present invention can produce antibodies with much smaller amounts of antigen in comparison with the conventional art of antibody production using animals (less than or equal to 1 μg. Animals are normally immunized with several mg.), and a large reduction in the time for production is possible (1 week at the shortest. In animals, several weeks are needed for polyclonal antibodies, and several months are needed for monoclonal antibodies.) Further, from a reduction in personnel costs due to the reduction in production time, it is possible to greatly lower the costs needed for the production of hybridomas for monoclonal antibodies. Additionally, since this is a system using cultured cells, there is an advantage in that even if a factor is toxic at the individual organism level, if it is non-toxic at the cellular level, it is usable as an antigen.

Additionally, as a method of producing antibodies in vitro, the phage display method and the like are conventionally known, but these methods use libraries wherein single strands made by connecting variable region genes for antibody heavy chains and light chains by linkers are incorporated into phagemids. Since natural antibodies, except for the variable region, have extremely different structures, in order to actually make antibodies, it is necessary to clone genes again from selected phages, and to connect them to the constant region of antibodies. On the other hand, in the method according to the present invention, since they are already in the form of IgM, they are in a state in which they are usable immediately in the form of antibody molecules. It is possible to follow publicly known methods for subsequent manipulation, and, for example, by using already existing secondary antibodies and the like, isolation, purification, and the like may be performed.

Further, in normal in vitro methods (such as phage display), the quality of the library (for example, the number of clones) is important, and great trouble is expended in library production. In addition to this, since the performance of libraries goes down as they are used repeatedly, their maintenance is not easy.

In the method according to the present invention, the production of a library with simple manipulation of a culture is possible, and since the produced library itself diversifies by itself, it can be maintained and managed as a normal cell culture. Additionally, in the phage display method, there are often cases where screening must be done several times, but in the method according to the present invention, it is possible to obtain a specific antibody with one screening, so it is possible to obtain a specific antibody easily and quickly.

For the immunocytes that can be used in the present invention, any cell is usable as long as it is a cell wherein somatic homologous recombination occurs at an antibody locus, but DT40 cells that are B cell lines derived from chickens are preferably used.

For the means to relax the chromatin structure, it is thought that any means that is publicly known to persons skilled in the art may be used, but a process wherein histone deacetylase inhibitor is put into contact with the target cells may be preferably used. This inhibitor may be any inhibitor that inhibits histone deacetylase, but trichostatin A is preferably used.

Additionally, when putting immunocytes into contact with histone deacetylase inhibitor as a method for relaxing the chromatin structure, any treatment concentration and treatment time may be used for the histone deacetylase inhibitors, as long as they are in a range wherein the contacted cells do not die. Concretely, in the case of trichostatin A, a treatment concentration of approximately 0.5 ng/ml to approximately 5.0 ng/ml is preferred, and a treatment time of approximately 2 weeks to approximately 2 years is preferred.

Still further, in the present invention, a medicinal agent for promoting somatic homologous recombination at a genetic locus, and comprising an inhibitor for histone deacetylase, is provided.

As the medicinal agent in the present invention, any inhibitor is usable as long as it is an inhibitor for histone deacetylase, but trichostatin A is the most commonly used, and preferred.

BRIEF DESCRIPTION OF THE DRAWINGS

FIG. 3 shows the influence of trichostatin A on homologous recombination.
(a) shows the diversity of an antibody light chain gene variable region of clones cultured for 3 weeks in the presence of 1.25 ng/ml trichostatin A.
(b) shows the diversity of an antibody light chain gene variable region of clones (No. 1-No. 6) cultured for 3 weeks in the absence of trichostatin A.

FIG. 5 shows the antigen specificity of cells selected with goat IgG magnetic beads.
(a) shows binding of cells to goat IgG after selection with goat IgG magnetic beads. Left: shows results for binding to goat IgG-FITC of a population of cells on which selection was not performed (unselected). Center: shows results for a clone that show strong binding to goat IgG (clone No. 3). Right: shows results for a clone that only shows extremely weak binding to goat IgG (representative example only, clone No. 17).
(b) shows binding to other antigens for a clone (No. 3) that shows strong binding to goat IgG. Top: shows binding results to streptavidin (SA). On the left is the population of cells for which selection was not done (SA, unselected), and on the right is shown the results for a clone that binds to goat IgG (SA, clone No. 3). Bottom: shows binding results to ovalbumin-FITC(OA). On the left is a population of cells for which selection was not done (OA, unselected), and on the right is shown the results for a clone (SA, clone No. 3) that binds to goat IgG.

FIG. 6 shows the analysis results for cells on which selection was performed using human IgG magnetic beads.
(a) The binding to human IgG-FITC for cells for which a strong signal was seen in the ELISA method. Shows results for 3 representative clones (clone7, clone8, clone20).
(b) Shows results when binding specificity in relation to the 3 clones shown in (a) is considered. Shows results of staining with human IgG-FITC (hIgG), rabbit IgG-FITC (rIgG), goat IgG-FITC (gIgG), streptavidin-FITC (SA), ovalbumin-FITC (OA), and analysis by FACS. "Unstained" refers to those that have not been stained.

(c) Results of ELISA on cell culture supernatant. For clone7, clone20, and unselected cells, the ELISA method was done using immunoplates coated with human IgG (hIgG), rabbit IgG (rIgG), goat IgG (gIgG), streptavidin (SA), and ovalbumin (OA). The culture supernatant was diluted from 1- to 500 000-fold dilution.

BEST MODE FOR CARRYING OUT THE INVENTION

Since the antibody production method of the present invention partly utilizes a method for promoting somatic homologous recombination, the antibody production method shall be described in detail.

As previously described, in the antibody production method of the present invention, immunocytes in which DNA homologous recombination at antibody loci is occurring are selected and cultured, and when producing antibodies, by manipulation so as to relax the chromatin structure of chromosomes of said immunocytes, the frequency of DNA homologous recombination occurring at the antibody locus is greatly improved, and in this way diverse antibodies are obtained.

Accordingly, herebelow, cell culture, the induction of chromatin structure relaxation, confirmation of chromatin structure relaxation, confirmation of homologous recombination, and confirmation of antibody expression shall be explained in order.

Cell Culture:

"Immunocytes" in the present invention refer to B cells that have antibody production ability, and types of host animals include mice, sheep, rats, and chickens (Honjo, T., Alt, F. W. (1995) Immunoglobulin Genes, $2^{nd}$ Edition (Academic Press)). Preferably established cell lines should be used, and particularly preferably DT40 cells should be used as the immunocytes.

"DT40 cells" are an established cell culture of B cells derived from chickens, and some modification (for example, recombination, insertion, deletion and the like of specific genes) has been done to the chromosomes possessed by said cells. Derivative cell lines and sublines are included.

The culture conditions for the cells used in the present invention are determined according to publicly known methods in said technical field, but needless to say, this shall be done in a medium and medium conditions (incubation temperature, $CO_2$ concentration) appropriate for the selected immunocytes. Therefore, in cases where the selected immunocyte is DT40, for example, IMDM (Ivitrogen) is used for the medium, and the conditions are an incubation temperature of for example 39.5 degrees C. and 5% $CO_2$ concentration. Culturing is done while keeping the cell concentration constant, and the existence or non-existence of somatic homologous recombination in the target cell antibody locus is confirmed at appropriate intervals of time (for example, daily or weekly).

Induction of Relaxation of Chromatin Structure at Antibody Loci of Immunocytes:

"Relaxation of the chromatin structure" as used here refers to the loosening of the chromatin structure of the entirety of the target locus, in order for each factor that is involved in homologous recombination to directly or indirectly act upon said locus (here, the antibody locus). Among factors that induce "relaxation," histone acetyltransferase (HAT), histone deacetylase inhibitors, chromatin structure modifying factors (for example, Swi/Snf Protein, Iswi Protein, and homologs thereof, and functional complexes thereof) are included. A factor that induces preferable "relaxation" is histone deacetylase inhibitor.

As the "histone deacetylase inhibitor," it is thought that any such inhibitor is usable as long as it is known by persons skilled in the art, such as protein factors such as antibodies that have histone deacetylase (HDAC) activity suppressing activity, trichostatin A, and small molecule compounds such as butylate and valproate, but most preferably, trichostatin A is utilized.

In order to relax the chromatin structure at an antibody locus of an immunocyte, the factor that induces relaxation is made to be expressed inside the target immunocyte, or is put into direct contact with said cell. In the cases where the factor that induces relaxation is a protein factor, and in cases where relaxation of the chromatin structure is induced by making said factor be expressed within the cell, this is accomplished by transfecting the target cell with appropriate promoters, terminators, enhancers, and the like for the expression of said factor in the target cell. It is possible for persons skilled in the art to carry out easily the expression of said factors inside immunocytes (See Spector, D. L., et al. (1998). Cells a Laboratory Manual (Cold Spring Harbor Laboratory Press)). In cases where the factors for inducing relaxation are directly contacted with the target immunocytes, culturing is done while keeping the concentration of said factors constant. Cells for which the factor that induces relaxation has been expressed or has been contacted are incubated for an appropriate amount of time to cause somatic homologous recombination at the antibody locus. For example, in cases where said factor is the histone deacetylase inhibitor trichostatin A, the appropriate amount of time to cause somatic homologous recombination at an antibody locus is preferably approximately 2 weeks to approximately 2 years, more preferably approximately 2 weeks to approximately 6 weeks, and most preferably approximately 5 weeks, and the appropriate concentration is preferably approximately 0.5 ng/ml to approximately 5.0 ng/ml, and most preferably, 1.25 ng/ml.

Detection of Changes in Chromatin Structure at Antibody Locus:

Changes in the chromatin structure at specific locus regions are generally detected using DNase sensitivity of said region as an indicator. In cells processed with the methods described above, when the chromatin structure of the target locus region relaxes, it is thought that decrease of the interaction between the DNA at that portion and the chromatin related protein (such as histone) occurs. As a result, the DNA region that was not digested by DNase because it was bound to the chromatin related protein becomes sensitive to DNase because of decreased interaction due to the relaxation of the chromatin structure. The change in the sensitivity to DNase from the time before and after the change in the chromatin structure alters the DNA cleavage pattern of said region, and by detecting newly generated DNA fragments by Southern blot and the like, it is possible to confirm the locus region for which the chromatin structure is relaxed. Here, as the DNase, DNaseI, MNase (micrococcal nuclease) are generally used.

Confirmation of Somatic Homologous Recombination at an Antibody Locus:

Confirmation of somatic homologous recombination is carried out by determining the genomic sequence of the antibody locus region of the cell on which the process using the method described above is performed, and comparing it to the genomic sequence of the antibody locus region of control cells on which the process described above is not performed. As the determination method for the genomic sequence of antibody locus regions, generally, said gene region is amplified with a specific DNA primer, and the amplified DNA fragments are sequenced by cloning into an appropriate sequencing vector. A simple method is to prepare a DNA primer that is necessary for amplifying the antibody locus region of the genomic DNA prepared from the target immunocytes (for example, in order to include the entire target antibody locus region, a primer in the positive direction is constructed in the vicinity of the 5' side of said gene, and a primer in the opposite direction is constructed on the 3' side of said gene) is prepared, and the antibody locus region is amplified by PCR. The antibody locus region that is amplified is either an antibody light chain gene and/or an antibody heavy chain gene and the variable region of either gene is preferred. For the DNA polymerase used for amplification, a commercially available one may be used, but preferably, one should be used for which the elongation of long DNA chains is possible, and fidelity is high. The conditions for performing amplification of the antibody locus region depends on the annealing temperature of the DNA primer used, and properties of the DNA polymerase used, but for example, after reaction at 98 degrees C. for 2 minutes, 30 seconds at 98 degrees C., 30 seconds at 57 degrees C., 1 minute at 72 degrees C. for 27 cycles, and then further reaction at 72 degrees C. for 15 minutes. Amplification products after reaction are separated by agarose gel electrophoresis, the DNA band containing the target antibody locus region is cut out, and after the DNA is recovered, it is cloned in a vector for sequencing. The sequencing vector may be any vector used in said technical area, but for example, pCR2.1-TOPO (Invitrogen) and the like are used. The frequency of somatic cell recombination is measured by analyzing the DNA sequence of the antibody locus region in the abovementioned prepared sequencing vector, and comparing it to the corresponding sequence derived from cells in which somatic homologous recombination at an antibody locus has not been induced.

Confirmation of Antibody Expression:

Confirming whether expression of the antibodies has actually been induced in the cells for which somatic homologous recombination at antibody locus has been confirmed according to the above description.

"Diverse antibodies" include IgA, IgD, IgE, IgG, IgY, and IgM.

(i) Confirmation of Secreted Antibodies

In cases where the antibody derived from the locus at which somatic homologous recombination was secreted, the existence of the target antibody molecules is confirmed in culture supernatant containing produced antibody molecules. As the method for confirmation, it is possible to perform this by any method publicly known to persons skilled in the art, but for example, a detection method using antibodies that specifically recognize produced antibody molecules (for example), using labeled secondary antibodies, such as Western blot or ELISA) is common. A simple way is to use culture supernatant as is in Western blot, ELISA, or the like. In cases where the concentration of produced antibodies is low, the confirmation of produced antibodies may be done after concentrating the target antibodies from said culture supernatant. A simple way is to concentrate and precipitate the antibody molecules from said culture supernatant by ammonium sulfate precipitation (50% ammonium sulfate) or the like, subsequently suspending an antibody molecule pellet in an appropriate buffer (for example), PBS and the like), and performing dialysis on this buffer. Dialysis is performed until ammonium sulfate is removed, while exchanging the dialyzing fluid. Detection of produced antibody molecules is done directly or indirectly by Western blot on the obtained antibody molecules using antibodies that specifically recognize said antibody molecules. Alternatively, in cases where the produced antibodies are IgG, confirmation can be done by direct purification by affinity chromatography using protein A or Protein G.

(ii) Confirmation of IgM Expressed on Cell Membranes

In cases where the antibodies produced by promoting somatic homologous recombination is IgM that is presented on cell membranes, confirmation can be done by fluorescent activated cell sorter (FACS) analysis using anti IgM antibodies.

Herebelow, embodiments shall be shown, but the present invention is not restricted to these.

Embodiment 1

Analysis of Chromatin Structure in DT40 Cell Antibody Locus Region after Trichostatin A (TSA) Treatment Whether an alteration of the chromatin structure of the antibody light chain gene has actually been produced by TSA was analyzed using indirect end labeling with micrococcal nuclease (MNase) sensitivity as an indicator. Among chicken antibody alleles, one is VJ rearranged and the other one is not rearranged, but it is known that actually functional in antibody production is VJ rearranged one. However, since both sequences are almost identical, it is difficult to analyze VJ rearranged allele of wild type DT40 cells by simple application of indirect end labeling method. In order to solve this problem, on the side for which VJ recombination has not occurred, a mutant of which sequences in the vicinity of the region to be used as a Southern hybridization probe is deleted is generated, and an analysis of MNase sensitivity using this mutant was performed.

Figure 1:
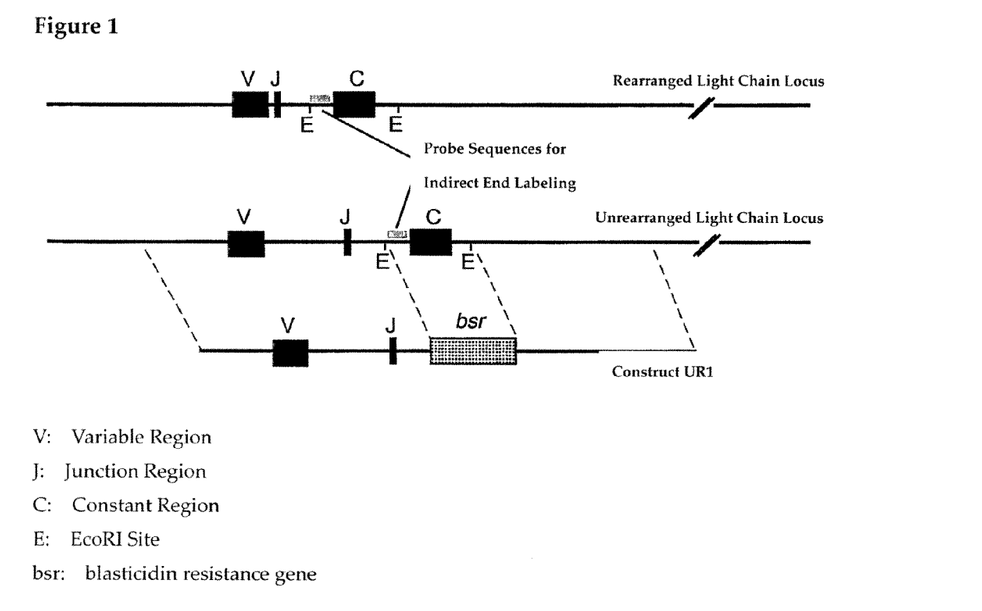
FIG. 1 is a view showing a frame format of the production of a variant with constant region and probe region for Southern hybridization deleted. Using a plasmid (Construct UR1) with a blasticidin resistance gene inserted, the vicinity of the constant region (including probe region) of an unrearranged light chain locus is replaced with a blasticidin resistance gene.

Generation of Deletion Mutant:

Plasmid #18-4 (obtained from Professor Shunnichi Takeda, Kyoto University Faculty of Medicine) cloned from an antibody light chain gene was digested with EcoRI, and among the two fragments produced, the larger fragment and a blasticidin resistance gene (obtained from Professor Takeda) fragment were ligated, and transformed into E. coli bacteria. In this way, the constant region and a region including the region to be used as a probe in Southern hybridization was deleted, and a plasmid (UR1) in which a blasticidin resistance gene is inserted instead was obtained (FIG. 1). Approximately 20 μg of this plasmid was digested with XbaI and straightened, infected into DT40 cells according to already known methods (Buerstedde, J. M., Takeda, S. Cell. 1991 67 (1):179-88), and a DT40 cell line (3H12) with a deletion mutation was introduced.

Isolation of Nuclei:

After culture fluid containing $10^7$-$10^8$ 3H12 cells incubated for 8 hours in a medium with TSA (0 ng/ml, 0.625 ng/ml, 1.25 ng/ml, 2.5 ng/ml) added was centrifuged at 300 g for 15 minutes, and the cells were recovered, this was suspended in 10 ml of PBS, centrifuged again at 300 g for 15 minutes, and recovered as pellets. Subsequently, the cells were suspended in 4 ml Nuclear Buffer (10 mM Tris-HCl (pH 8.0), 0.32M Sucrose, 5 mM $MgCl_2$, 1% TritonX-100, 0.5 mM DTT, 0.1 mM PMSF), and subsequently the cell membranes were removed by leaving on ice for 15 minutes. Nuclei were recovered by centrifuging for 5 minutes at 1000 g.

MNase Digestion:

The nuclear pellet was resuspended in 10 ml RSB (10 mM Tris-HCl (pH7.5), 10 mM NaCl, 1.5 mM $MgCl_2$, 0.5 mM DTI. 1 mM PMSF). Nuclei were recovered by centrifuging again at 1000 g for 5 minutes, and suspended in 400 ml of RSB. The DNA concentration of this nuclear suspension was measured by Hoechst 33258 binding, and suspension corresponding to 100 µg was made into 500 ml with RSB. Four of these were prepared for each cell. 0.5 µl of 1 M $CaCl_2$, and MNase (0 U, 0.04 U, 0.2 U, 1 U) was further added, and after digestion for 5 minutes at 37 degrees C., 20 µl of 0.5 M EDTA and 12.5 µl of 20% SDS, 2 µl of 15 mg/ml proteinase K was added, and reacted overnight at 50 degrees C. 500 µl of phenol chloroform was added, and after gently agitating for 30 minutes, centrifuged for 30 minutes at 1.5 Krpm, the upper layer was recovered, and transferred to a new tube. 500 µl of chloroform was further added and this was agitated again for 30 minutes, and after centrifuging for 5 minutes at 1.5 Krpm, the upper layer was transferred to a new tube. 50 µl of 3M sodium acetate and 1 ml of cold ethanol was added, and mixed gently. Centrifuging was done for 20 minutes at 1.5 Krpm, and after the supernatant was removed, 500 µl of 80% ethanol was added and mixed gently, and this was centrifuged again for 5 minutes at 1.5 Krpm. After the supernatant was removed, the precipitate was air dried. 100 µl of TE (10 mM Tris-HCl (pH8.0), 1 mM EDTA) was added to this, kept at 55 degrees C. for 1 hour, and subsequently dissolved by leaving overnight at 4 degrees C.

Southern Blot Analysis:

Southern blot analysis was done by the method of Church and Gilbert (Church, G. M., Gilbert, W. Proc. Natl. Acad. Sci. USA 1984 81 (7):1991-5). After approximately 20 µg of DNA was purified by spin column (Pharmacia ProbeQuant G-50), this was digested with the restriction enzyme BsaAI (NEB). Subsequently, phenol/chloroform extraction was done, and after DNA was recovered from the ethanol precipitate, electropheresis was done with a 1.5% agarose gel in a TAE (40 mM Tris-acetate, 1 mM EDTA) buffer. DNA was transferred to a membrane by a Vacu Gene XL nucleic blotting system (Pharmacia). First, denaturing was done for 15 minutes with denaturing buffer (1.5 M NaCl, 0.5 M NaOH), then transfer was done over 4 hours with transfer buffer (1.5 M NaCl, 0.25 M NaOH). After the membrane was neutralized with 20×SSC, prehybridization was done for 1 hour at 62 degrees C. with a hybridization buffer (10 mg/ml BSA, 0.5 M $Na_2PO_4$ (pH7.4), 7% SDS, 1 mM EDTA). Subsequently, 50 ng of probe labeled with $[\alpha^{32}P]dCTP$ was hybridized overnight at 62 degrees C. in a hybridization buffer. Subsequently, the membrane was washed for 10 minutes at 62 degrees C. with 50 ml of Wash Buffer (20 mM $Na_2PO_4$ (pH7.4), 1% SDS, 1 mM EDTA) preheated to 65 degrees C., and after this step was further repeated for 4 times, the radiation activity of the membrane was analyzed with a BAS 2000. The probe DNA was produced using the PCR method (Roche, Expand Hi Fidelity PCR system). At that time, ATCTTGCCTTCCT-CATGGC (Sequence Number 1) and GTTTGGGT-GAACGTGGTTC (Sequence Number 2) were used as primers, and a Plasmid #18-4 which is a clone of a chicken antibody light chain gene was used as the template.

Figure 2:
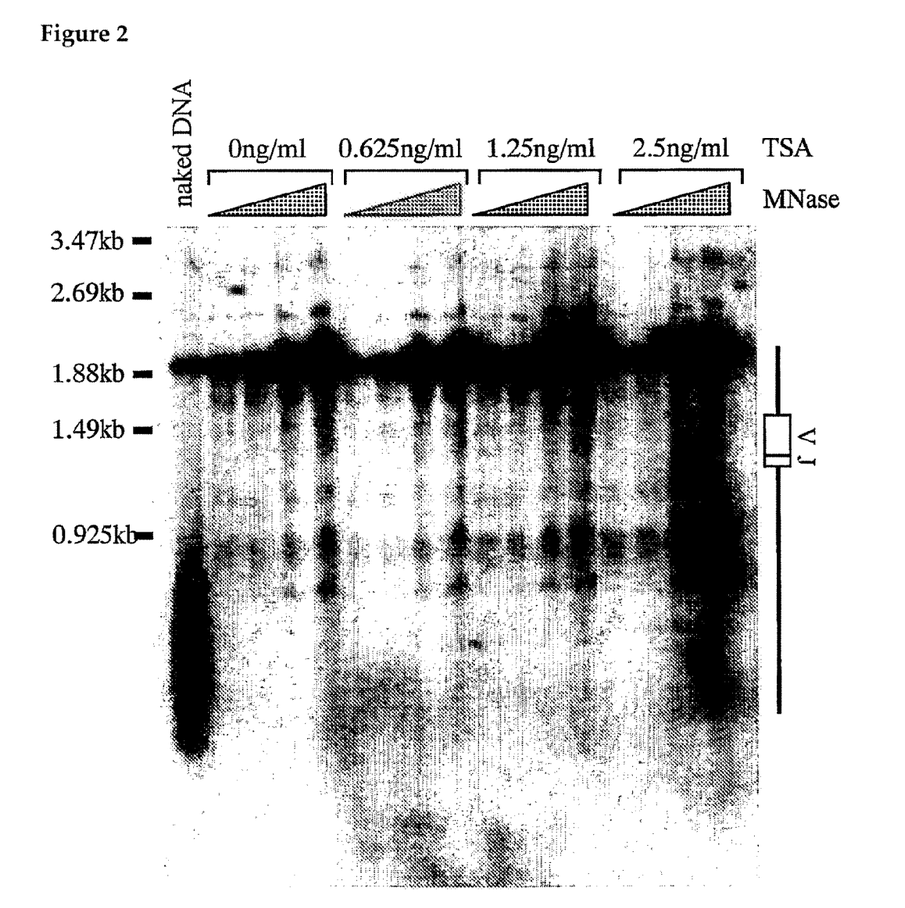
FIG. 2 shows the increase in TSA dependent accessibility of the antibody light chain gene chromatin structure. Naked DNA refers to the same region of deproteinized genomic DNA.

Results:

When the added MNase amount (0 U, 0.04 U, 0.2 U, 1 U) was increased under various concentrations of TSA (0 ng/ml, 0.625 ng/ml, 1.25 ng/ml, 2.5 ng/ml), with the increase in TSA concentration and MNase amount, it was confirmed that DNA fragments that are generated by the cleavage of the VJ region appear (Comparison with FIG. 2, bands at locations indicated by "VJ", for example the $5^{th}$ lane and $17^{th}$ lane from the left). Since these bands were not detected when MNase amount was increased in the absence of TSA (0 ng/ml) (FIG. 2, $5^{th}$ lane from left), this indicates that in order for the VJ region to be cleaved by MNase, TSA must be present. From the above results, it was confirmed that the chromatin structure of the VJ regions of DT40 cell lines were relaxed by TSA, and the accessibility of MNase to those regions increased.

Embodiment 2

Confirmation of Promotion of Somatic Homologous Recombination at Antibody Locus of DT40 Cells by Trichostatin A (USA)

Cell Culture

DT40 cells were incubated at 39.5 degrees C. in a $CO_2$ constant temperature oven in 5% $CO_2$. IMDM medium (Invitrogen) was utilized as the medium, with 10% FBS, 1% chicken serum, 100 units/ml penicillin, 100 µg/ml streptomycin, and 55 µM 2-mercaptoethanol added. Additionally, for trichostatin A (Wako Pure Chemical Industries), this was dissolved to 5 mg/ml in methanol for stock, and this was used by diluting in an appropriate medium until the final concentration was 1.25 ng/ml.

DT40 cells that do not express IgM on their cell surfaces (herebelow, IgM(−) cells) were diluted to approximately 20 cells/ml and 100 µl each was pipetted into a 96 well plate. At this time, a medium with 1.25 ng/ml trichostatin A added, and a medium with this not added, were prepared. This was incubated until single colonies appeared, and 5 clones (For No TSA, 6 clones) were transferred to a 6 well plate with 2 ml of fresh medium inside. At this time, incubation was continued by maintaining the original TSA concentration, and maintaining the cell concentration at $10^5$-$10^6$ cells/ml.

Extraction of Genomic DNA:

With the abovementioned method, live cells of DT40 that were incubated for 3 weeks were recovered by fluorescence-activated cell sorter. With an EPICS ELITE ESP, 100 000 live cells were collected in a 1.5 ml tube. Cells suspended in the sheath fluid were recovered by centrifuge (1000 g, 10 min), 300 µl of genomic extraction buffer (100 mM Tris-HCl, pH8.0, 5 mM EDTA, 0.2% SDS, 200 mM NaCl, and 100 µg/ml Proteinase K) was added directly to the pellet, and digested overnight at 50 degrees C. The next day, 750 µl of ethanol was added, and mixing was done by gently turning upside down. Genomic DNA was recovered by centrifuge (1000 g, 10 min), washed with 70% ethanol, and dried. 100 µl of TE buffer (10 mM Tris-HCl, pH8.0, 1 mM EDTA) was added to this, and after leaving for 30 minutes at 50 degrees C., this was dissolved overnight at 4 degrees C.

Figure 3:
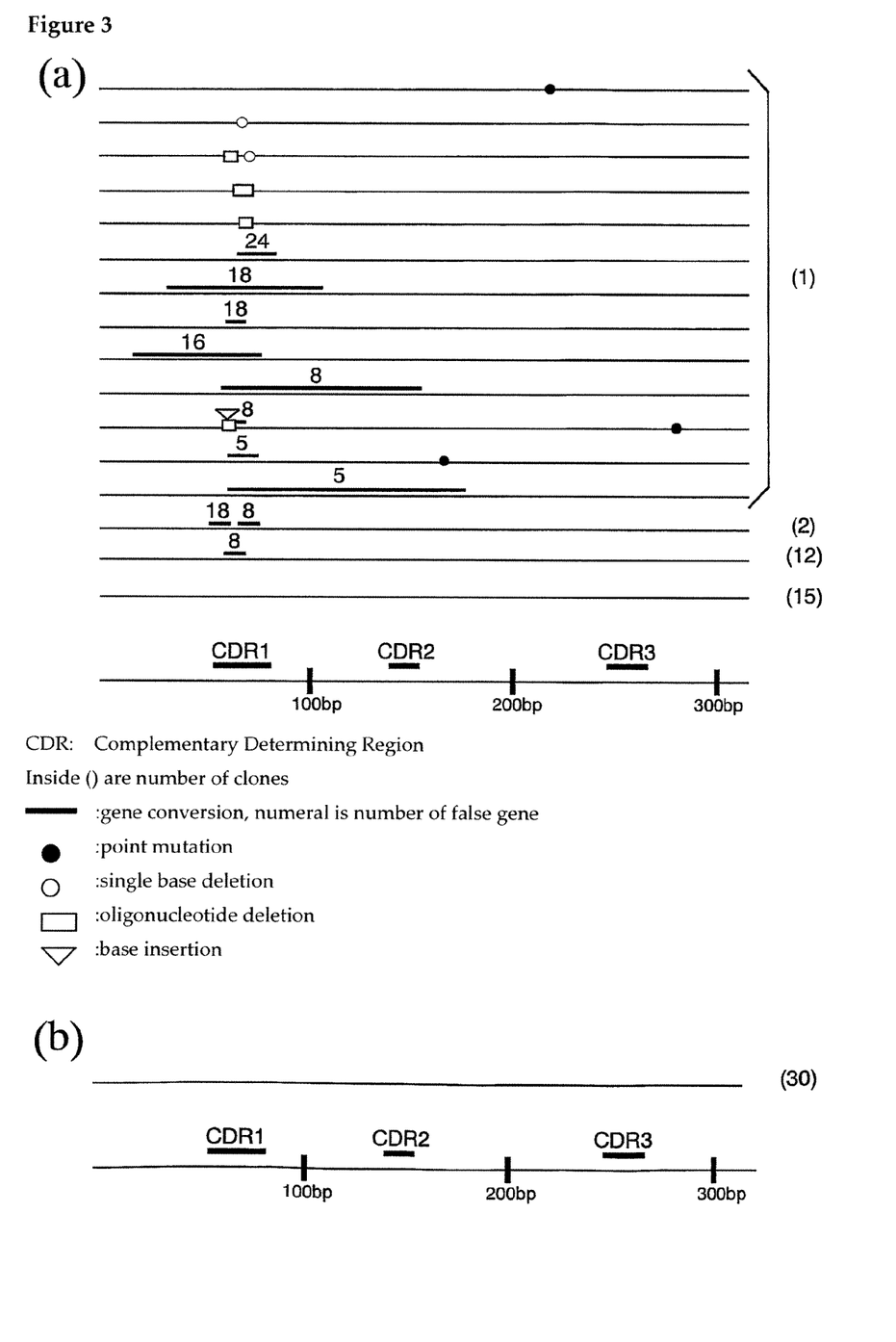

Analysis of Sequence of Antibody Light Chain Gene Variable Region:

PCR (Perkin Elmer 9600) was utilized for the amplification of the antibody light chain gene variable region. 5 µl of genomic DNA solution (corresponding to 5000 cells) was used as the template, and as primer, 10 pmol of upstream (CACACCTCAGGTACTCGTTGCZG (Sequence Number 3)), and downstream (TCAGCGACTCACCTAGGACGG (Sequence Number 4)), respectively, were used. Using Pyrobest DNA Polymerase (Takara Shuzo), reaction was done at the 50 µl scale. The reaction conditions were such that after 2 minutes at 98 degrees C., 30 seconds at 98 degrees C., 30 seconds at 57 degrees C., 1 minute at 72 degrees C., and this was done for 27 cycles, and finally, reacting was done for 5 minutes at 72 degrees C. Subsequently, 1 µl of ExTaq DNA Polymerase (Takara Shuzo) was added, and after reacting for 15 minutes at 72 degrees C., 20 µl from the entire reaction fluid was separated by agarose gel electrophoresis. The bands that correspond to the light chain gene were cut out, and after DNA was recovered with a Gel Extraction kit (Qiagen), this was cloned into a pCR2.1-TOPO vector with a TOPO TA Cloning kit (Invitrogen), and transformed into *E. coli* bacteria. Plasmids were extracted, and the sequence was analyzed by an ABI PRI SM 377 DNA Sequencer (Perkin Elmer).
Result:
When the sequence of amplified antibody light chain gene variable regions cloned into plasmid vectors was analyzed, the results in FIG. 3 were obtained. In cells to which trichostatin A was added and cultured, 42 samples were sorted into 16 types (FIG. 3(a)). It was found that this diversity is generated from homologous recombination, gene insertion, gene deletion, and point mutations. On the other hand, in cells cultured in the absence of trichostatin A, after having analyzed 30 samples, homologous recombination was not found (FIG. 3(b)). From the above analysis results, it may be concluded that the diversity of antibody light chain genes of DT40 cell lines rose markedly due to the addition of trichostatin A.

Embodiment 3

Promotion of Appearance Frequency of IgM(+) DT40 Cells Due to Trichostatin A

Figure 4:
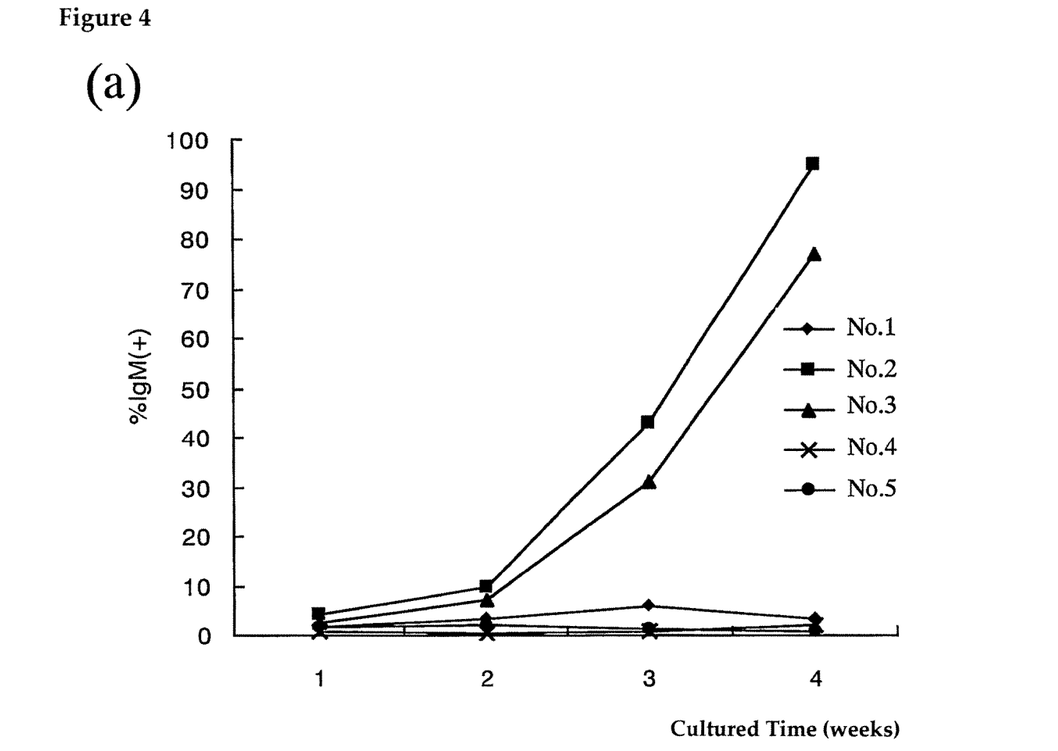
FIG. 4 shows the influence of trichostatin A on the frequency of appearance of IgM(+) cells.
(a) shows the results for 5 clones (No. 1-No. 5) cultured in the presence of 1.25 ng/ml of trichostatin A.
(b) shows the results for 6 clones (No. 1-No. 6) cultured in the absence of trichostatin A.

Confirmation of IgM Expression with a Fluorescence Activated Cell Sorter (FACS)
Culture fluid containing approximately $10^6$ IgM(−) cells on which trichostatin A treatment was done by the method described in Embodiment 2 was put in 1.5 ml tubes, said cells were recovered by centrifuging (1000 g, 5 minutes), and suspended in 200 µl of staining buffer (PBS, 0.3% BSA). The cells were recovered by centrifuging again, then suspended in 200 µl of FITC-labeled anti chicken IgM antibody (BETHYL) diluted to 1/250 fold with a staining buffer, and reacted for 1 hour on ice. The cells were recovered by centrifuging, then the cells were washed by suspending them again in 200 µl of staining buffer, and centrifuging this. After repeating this washing step one more time, the cells were suspended in 100 µl of staining buffer containing 5 µg/ml of propidium iodide (Nakarai). The fraction of cells expressing IgM was calculated by measuring 10 000 cells with an EPICS ELITE ESP (Beckman Coulter). At this time, cells stained by propidium iodide were gated out as dead cells.
Results:
When the fraction of cells expressing IgM (herebelow, IgM(+) cells) was measured every other week with FACS, as in FIG. 4, it was seen that the fraction of IgM(+) increased time dependently. It is thought that the IgM(+) cells were generated as a result of IgM(−) cells undergoing homologous recombination.

Embodiment 4

Selection of Antigen Specific Antibodies

Production of Antigen Magnetic Beads
Dynabeads M-280 Tosylactivated (Dynal) were used as magnetic beads, and coupling to antigens was done according to the manual. At this time, Dynal MPC (Dynal) was used as the magnetic stand. After 200 µl of beads was washed three times in 500 µl of Buffer A (0.1 M Na-Phosphate pH7.4), this was reacted while agitating by rotation for 24 hours at 37 degrees C. with 240 µg of goat IgG (SIGMA) or human IgG (SIGMA) in 400 µl of Buffer A. Next, the beads were washed 2 times in 500 µl of Buffer C (10 mM Na-Phosphate pH7.4, 150 mM NaCl, 0.1% BSA). Subsequently, 500 µl of Buffer D (0.2 M Tris-HCl pH8.5, 0.1% BSA) was added, reacted by agitating by rotation for 4 hours at 37 degrees C., and blocking was done. Subsequently, after washing 2 times in 500 µl of Buffer C, this was suspended in 400 µl of Buffer C containing 0.02% sodium azide.
Selection by Antigen Magnetic Beads:
Selection using antigen magnetic beads was done according to the method of Cumbers et al. (Cumber et al., Nat. Biotechnol. (2002) 20 (11):1129-1134). $5 \times 10^7$ wild type DT40 cells grown for 6 weeks or more in IMDM medium containing 1.25 ng/ml of trichostatin A was washed 2 times with 5 ml of selection buffer (PBS containing 1% BSA), and further washed with 1 ml of selection buffer. Subsequently, the cells were suspended in 1 ml of selection buffer, then added to 1 µl equivalent of antigen magnetic beads (washed 2 times in 1 ml selection buffer). This was reacted by agitation by rotation for 10 minutes at 4 degrees C. Subsequent treatment was slightly different depending on the type of antigen used, so these shall be explained separately.
(i) Selection Using Goat IgG Magnetic Beads
Cells for which selection was done with goat IgG magnetic beads were washed 3 times in 1 ml of selection buffer using a magnetic stand. Subsequently recovered cells were suspended in 500 µl of selection buffer, then added to 10 ml of IMDM medium, and 100 µl was pipetted into each well of a 96 well plate. The 96 well plate was maintained under 40 degrees C. heat inside a $CO_2$ incubator.
(ii) Selection Using Human IgG Magnetic Beads
Cells for which selection was done with human IgG magnetic beads were washed 3 times in 1 ml of selection buffer containing 2.5% Pluronic F68 (SIGMA) using a magnetic stand. Subsequently recovered cells were suspended in 500 µl of selection buffer, then added to 30 ml of IMDM medium, and 100 µl each was pipetted into each well of a 96 well plate. The 96 well plate was maintained under 40 degrees C. heat inside a $CO_2$ incubator.
Staining with Fluorescence Labeled Antigen:
Culture fluid containing $10^6$ cells derived from one well of the 96 well plate was put into a 1.5 ml tube, cells were recovered by centrifuging, and washed 2 times with 200 µl of selection buffer. Next, they were suspended in 200 µl of selection buffer with 10 µg/ml of FITC labeled antigens (goat IgG, human IgG, rabbit IgG (all from SIGMA) streptavidin (Dako), ovalbumin (Molecular Probes)), and reacted for 1 hour on ice. The cells were recovered by centrifuging, and washing was done by suspending again in 200 µl of selection buffer, and centrifuging. The fluorescence intensity of stained cells was measured by an EPICS ELITE ESP (Beckman Coulter).
ELISA:
ELISA was done according to the SOLID PHASE GUIDE (NalgeNunc). 200 µl of antigen solution (5 µg/ml in PBS) was added to each well of a Nunc-Immuno Plate MaxiSorp Surface (Nalge Nunc), this was reacted overnight at room temperature, and plate coating with antigens was done. The next day, the fluid inside the wells was removed, 200 µl of blocking buffer (PBS containing 0.5% skim milk) was added, and this was reacted for 1 hour. Subsequently, the wells were washed 3 times in 200 µl of ELISA washing buffer (PBS containing 0.05% Tween20). 100 µl of solution containing cell culture supernatant and the like, and antibodies was added to this, and reacted for 1 hour. Next, washing was done 5 times with 200 µl of ELISA washing buffer. For secondary antibodies, 100-200 µl of HRP labeled anti chicken IgM goat antibody (BETHYL) diluted 2000 times with PBS was added, and reacted for 1 hour. After secondary antibodies, washing was done 5 times with 200 µl of ELISA washing buffer. Color reaction was done with 100 µl of TMB+ (Dako), and the reaction was halted with 100 µl of 1 M sulfuric acid. Measurement was done by measuring 450 nm light absorption with a µQuant Biomolecular Spectrometer (Bio-Tek Instruments).

Production of Culture Supernatant for ELISA:

For culture supernatant for which the titer was analyzed by ELISA, in order to remove IgM and the like derived from serum, a medium prepared in the following way was used. Immunoglobulin was removed as precipitate from chicken serum (Invirtogen) by 50% saturated ammonium sulfate, and the supernatant was dialyzed against PBS. The volume increase due to dialysis was compensated for by concentration with Centri Prep (Amicon), and antibody removed chicken serum was made. This was added to AIM-V serum-free medium (Invitrogen) at a 3% concentration. Cells were added to this at a concentration of $10^6$ cells/ml, cultured for 2 days, the culture supernatant was removed, and ELISA was performed.

Figure 5:
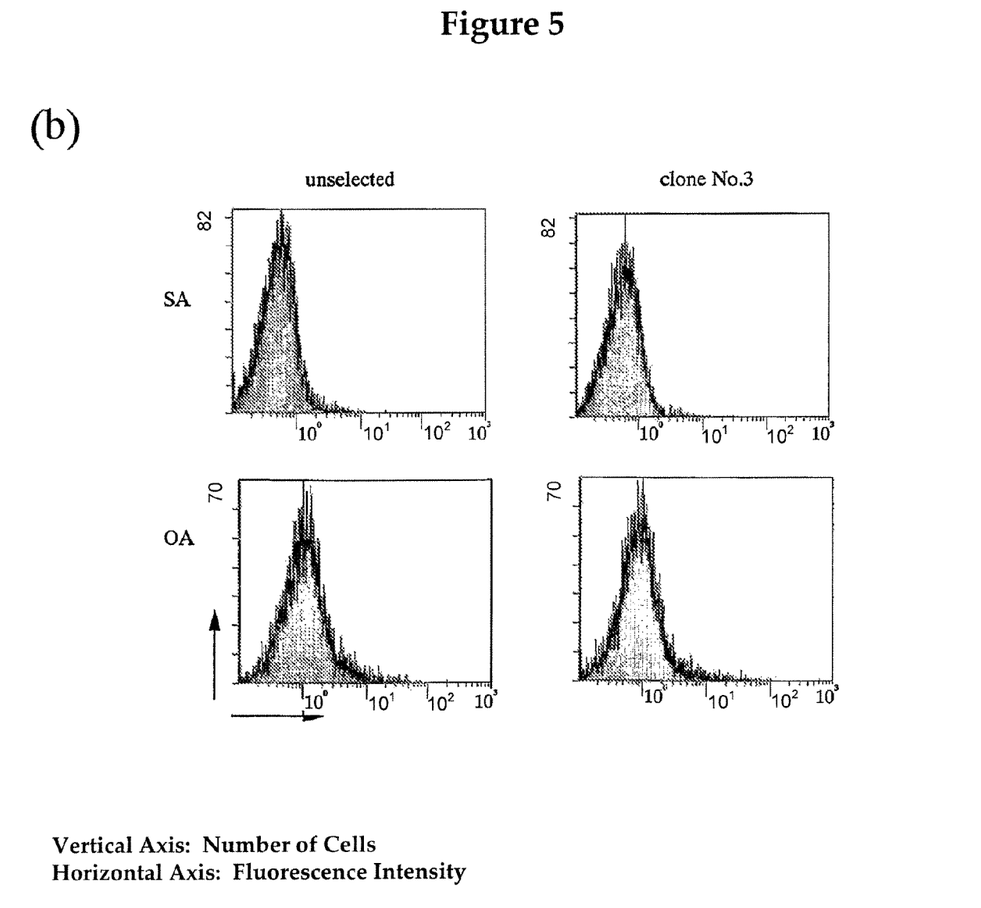
Figure 5A:
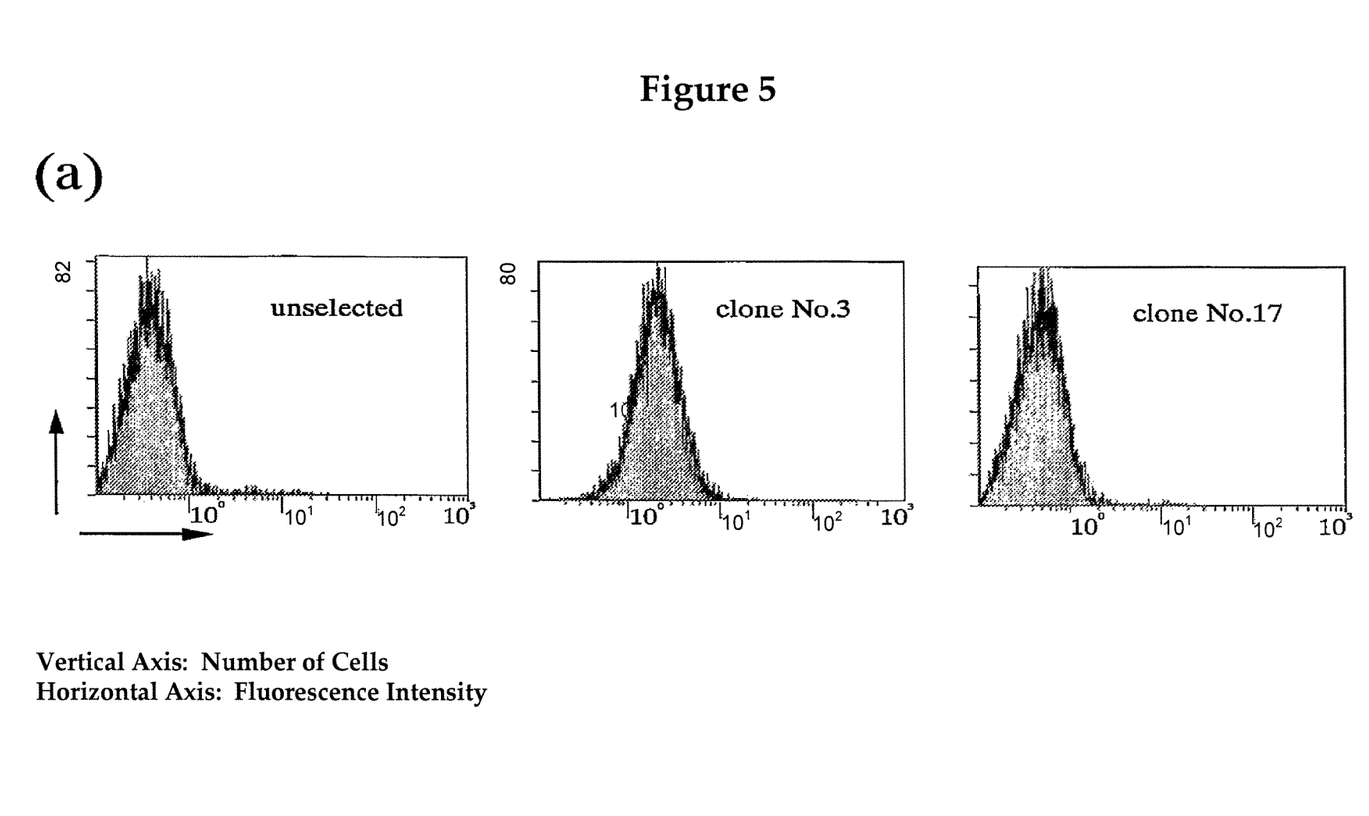

Results:

Selection was done on approximately $5\times10^7$ DT40 cells grown for 6 weeks in a medium containing 1.25 ng/ml Trichostatin A, using magnetic beads to which goat IgG was covalently conjugated, and selecting of cells that bind to goat IgG was attempted. Cells binding to the magnetic beads were pipetted into a 96 well plate and cultured. The antibody binding of cells derived from colonies that subsequently appeared was investigated. When binding to FITC labeled goat IgG was analyzed by FACS for 9 clones, for 1 clone, strong fluorescence was observed, suggesting binding between these cells and goat IgG (FIG. 5(a)). Next, in order to investigate whether this binding is specific, similar experiments were done with FITC-labeled streptavidin and ovalbumin. For both streptavidin-FITC and ovalbumin-FITC, an increase in fluorescence intensity was not observed, suggesting that binding between the cells and goat IgG is specific (FIG. 5(b)). It can be thought that the above results suggest that in IgM on cell surfaces that were diversified by trichostatin A treatment, ones that bind specifically to goat IgG were generated, and these were selected by the antigen magnetic beads.

Figure 6A:
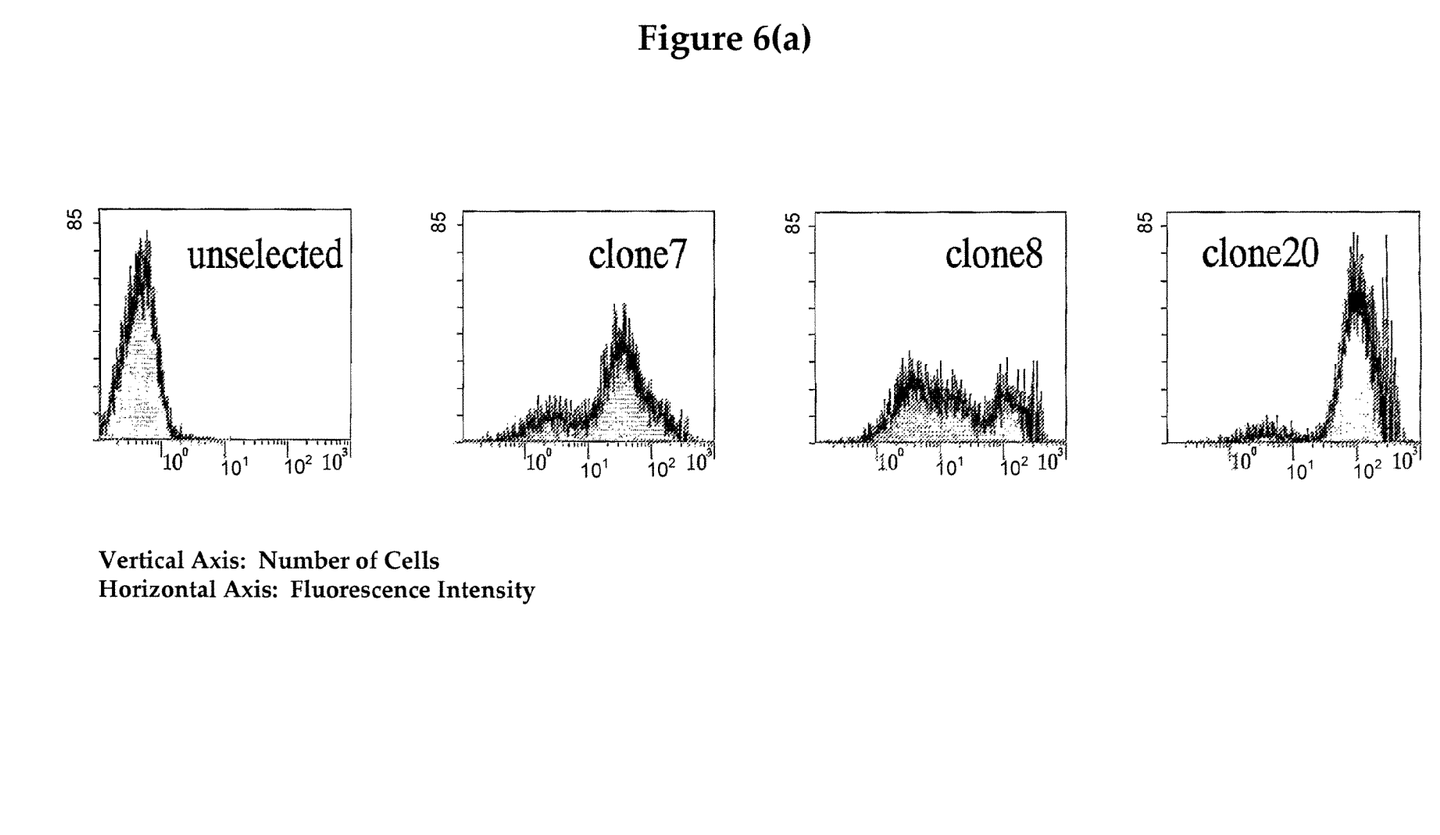

Next, in order to investigate whether it is possible to select cells that produce antibodies against antigens other than goat IgG, selection was done using human IgG magnetic beads. Here, in order to obtain positive clone candidates, ELISA was performed. Upon analysis with 100 µl of cell culture supernatant in a 96 well plate using immunoplates coated with human IgG, markedly strong light absorption was seen for culture supernatant derived from 14 wells. Next, the cells within these wells were cultured, stained by human IgG-FITC, and analyzed by FACS. Results for representative examples are shown in FIG. 6(a). For all of these, an increase in fluorescence intensity of several times at the lowest and several hundred times at the highest was found. Additionally, clones showing single peaks such as clone20 were seen, but others showing multiple peaks or a broad distribution such as clone7 or clone8 were also seen. When these cell populations having multiple peaks and broad peaks were cloned by limited dilution, clones showing distinct single peaks were obtained (data not shown). From this, it may be thought that clones showing patterns such as clone7 and clone8 are such that multiple positive clones existed in the same well in the 96 well plate.

Figure 6B:
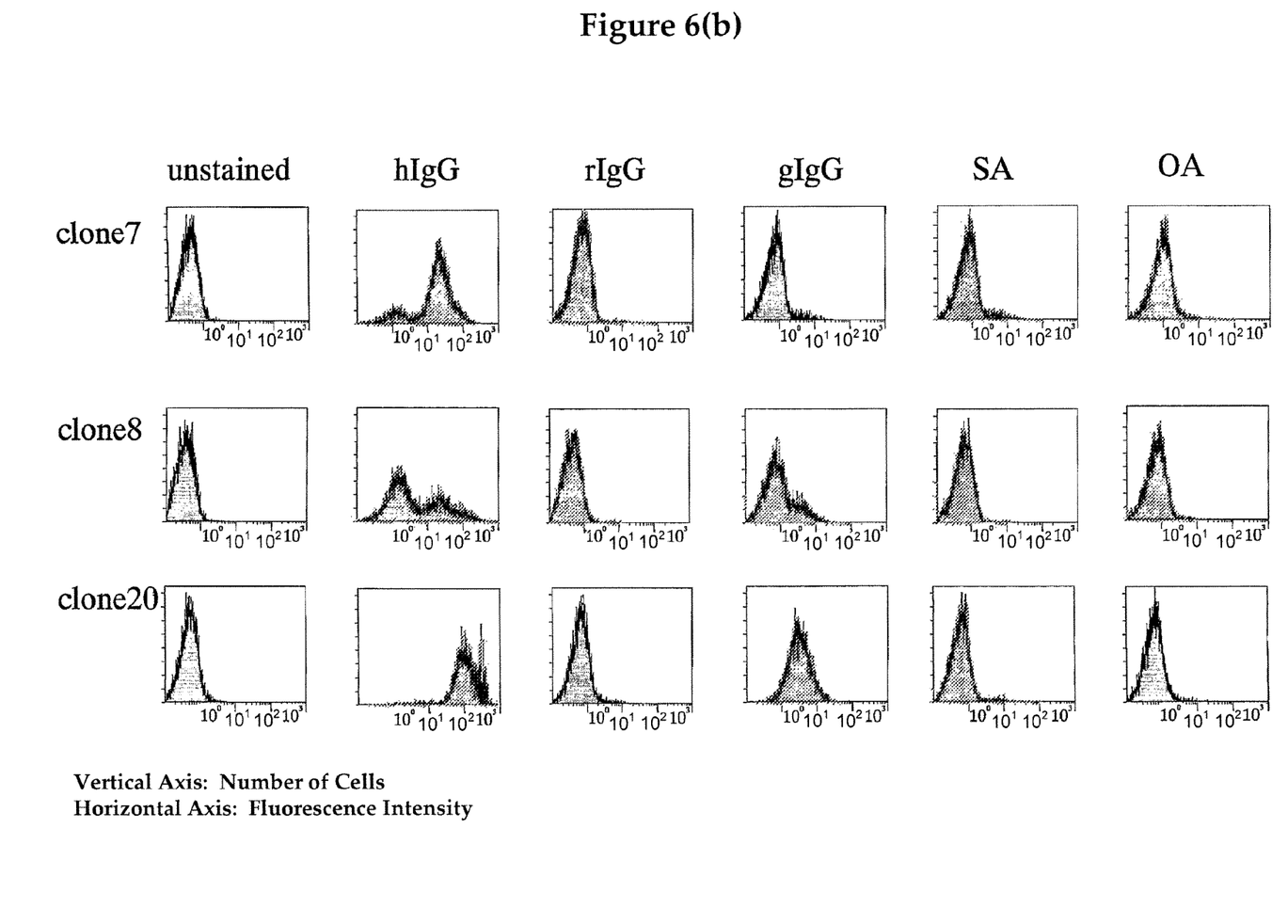

Next, antigen specificity was investigated for clone7, 8, and 20 (FIG. 6, (b)). Staining was done with human IgG-FITC, rabbit IgG-FITC, goat IgG-FITC, streptavidin-FITC, and ovalbumin-FITC, and analysis was done by FACS. With regard to clone7 and clone8, a distinct specificity against human IgG was seen. On the other hand, for clone20, slight binding to goat IgG was seen, and it was evident that crossover with homologs in other species occurs. No binding was seen for any clone to rabbit IgG, streptavidin, or ovalbumin.

Figure 6C:
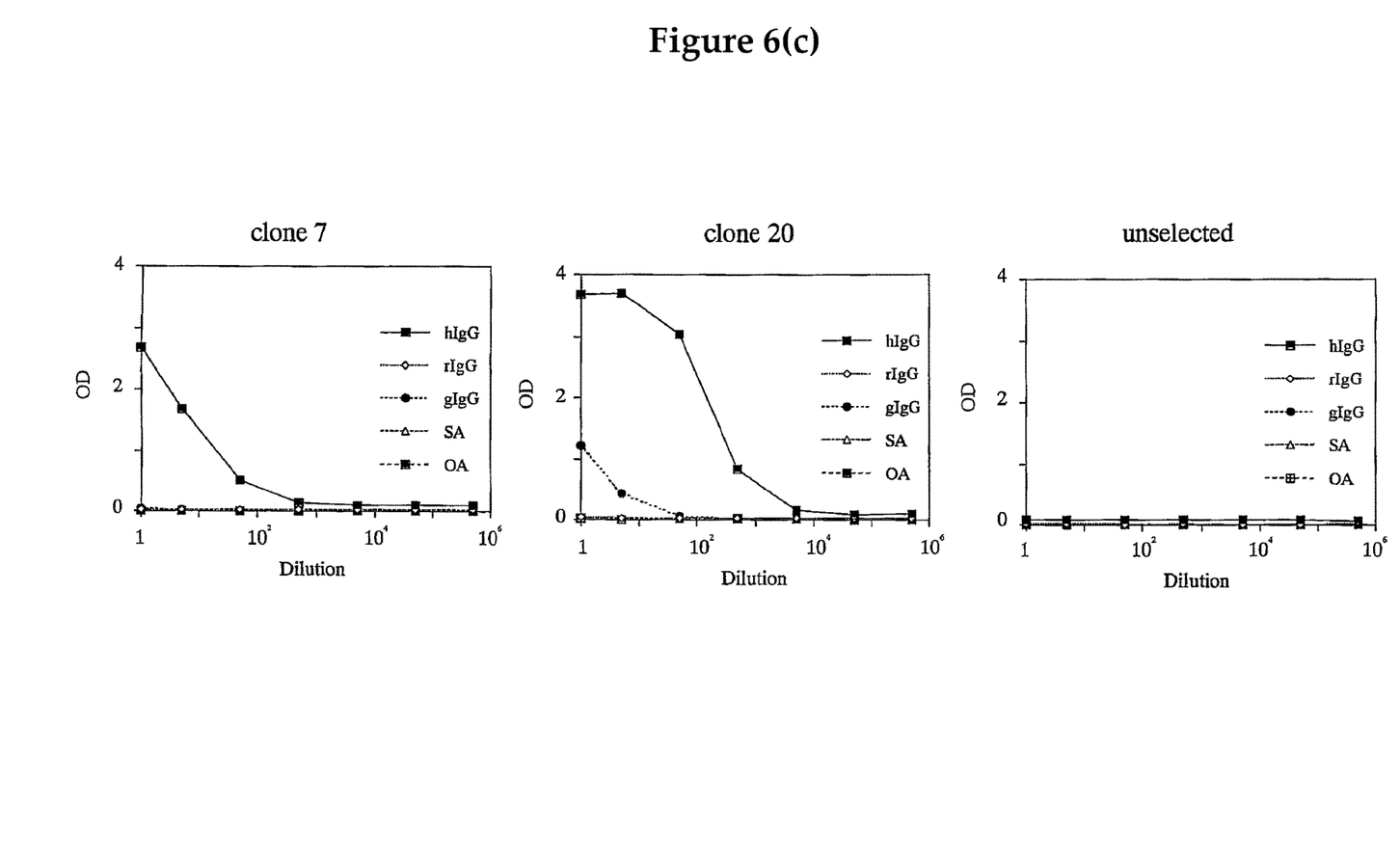

Further with regard to clone7 and clone20, ELISA was done using culture supernatant (FIG. 6(c)). When immunoplates coated with human IgG, rabbit IgG, goat IgG, streptavidin, ovalbumin were used, both clone7 and clone8 showed reactivity to human IgG, and significant signals were detected for clone7 up to 50 times dilution, and for clone20 up to 500 times dilution. Further, slight reactivity of clone20 to goat IgG was seen under FACS analysis (FIG. 6(b)), and reaction to goat IgG was also seen, albeit weakly, in ELISA, and this result agreed with the FACS analysis. Culture supernatant for cells for which selection was not done did not show a particular reaction against any antigen.

INDUSTRIAL APPLICABILITY

According to the method for promoting somatic cell recombination according to the present invention, the desired somatic homologous recombination can be induced and promoted under controlled conditions, thereby making their use for, for example, the production of protein factors possible.

Additionally, according to the antibody production method according to the present invention, diverse antibodies can be produced artificially using cultured cells.

Further, by utilizing an immunocyte cell line (US Patent A1 20020028488) created for the production of antibodies effective for treatment of specific diseases (for example, human antibodies, humanized antibodies and the like), diverse antibodies exhibiting greater treatment effects can be secured conveniently and continuously by the use of cultured cell systems.

The invention claimed is:

1. A method of producing a library comprising chicken-derived B cells making a diversity of monoclonal antibodies wherein each chicken-derived B cell makes a single monoclonal antibody, comprising
   a) providing chicken-derived B cells in which gene conversion is occurring at an immunoglobulin locus;
   b) contacting said chicken-derived B cells with an amount of a histone deacetylase inhibitor effective for relaxing chromatin structure of chromosomes in said chicken-derived B cells and enhancing gene conversion; and
   whereby diverse antibody producing chicken-derived B cells are obtained wherein each chicken-derived B cell makes a single monoclonal antibody.

2. The method according to claim 1, wherein the histone deacetylase inhibitor is trichostatin A.

3. The method according to claim 2, wherein the trichostatin A is present in a concentration of approximately 0.5 ng/ml to approximately 5.0 ng/ml, and the contact time is from approximately 2 weeks to approximately 6 weeks.

4. The methods according to claim 1, wherein the chicken-derived B cells are DT40 culture cells.

5. A method for producing a chicken-derived monoclonal B cell that binds a target antigen, comprising:

a) providing chicken-derived B cells in which gene conversion is occurring at an immunoglobulin locus;
   b) contacting said chicken-derived B cells with an amount of a histone deacetylase inhibitor effective for relaxing chromatin structure of chromosomes in said chicken-derived B cells and enhancing gene conversion;
   whereby diverse antibody producing chicken-derived B cells are obtained wherein each chicken-derived B cell makes a single monoclonal antibody;
   c) contacting said chicken-derived monoclonal B cells with the target antigen and
   selecting a chicken-derived B cell that produces an antibody that binds the target antigen.

6. The method according to claim 5, wherein the histone deacetylase inhibitor is trichostatin A.

7. The method according to claim 6, wherein the trichostatin A is present in a concentration of approximately 0.5 ng/ml to approximately 5.0 ng/ml, and the contact time is from approximately 2 weeks to approximately 6 weeks.

8. The methods according to claim 5, wherein the chicken-derived B cells are DT40 culture cells.

* * * * *